United States Patent [19]

Chang et al.

[11] Patent Number: 5,227,552
[45] Date of Patent: Jul. 13, 1993

[54] PROCESS FOR HYDROGENATING ALKENES IN THE PRESENCE OF ALKANES AND A HETEROGENEOUS CATALYST

[75] Inventors: Clarence D. Chang, Princeton, N.J.; Stuart D. Hellring, Yardley, Pa.; Randy F. Striebel, Mt. Holly, N.J.

[73] Assignee: Mobil Oil Corporation, Fairfax, Va.

[21] Appl. No.: 873,842

[22] Filed: Apr. 27, 1992

[51] Int. Cl.$^5$ .......... C07C 5/02; C07C 5/327; C07C 2/00; B01J 20/34
[52] U.S. Cl. .......... 585/257; 585/656; 585/700; 585/906; 502/180; 502/25; 502/27; 502/36; 502/53; 502/55
[58] Field of Search .......... 585/268, 656, 700, 906; 502/180, 25, 27, 36, 53, 55

[56] References Cited

U.S. PATENT DOCUMENTS

| Re. 28,398 | 4/1975 | Chen et al. | 208/111 |
|---|---|---|---|
| 3,321,545 | 5/1967 | Rigney et al. | 585/257 |
| 3,668,113 | 6/1972 | Burbidge et al. | 208/97 |
| 3,755,138 | 8/1973 | Chen et al. | 208/33 |
| 3,803,052 | 4/1974 | Hayes | 502/53 |
| 3,890,218 | 6/1975 | Morrison | 208/135 |
| 3,917,564 | 11/1975 | Meyers | 208/131 |
| 3,960,978 | 6/1976 | Givens et al. | 260/683.15 |
| 4,021,502 | 5/1977 | Plank et al. | 260/683 |
| 4,100,056 | 7/1978 | Reynolds | 208/57 |
| 4,100,218 | 7/1978 | Chen et al. | 260/673 |
| 4,150,062 | 4/1979 | Garwood et al. | 260/673 |
| 4,211,640 | 7/1980 | Garwood et al. | 208/255 |
| 4,227,992 | 10/1980 | Garwood et al. | 208/46 |
| 4,400,265 | 8/1983 | Shen | 208/97 |
| 4,438,288 | 3/1984 | Imai et al. | 502/36 |
| 4,456,781 | 6/1984 | Marsh et al. | 585/533 |
| 4,483,760 | 11/1984 | Tabak et al. | 208/60 |
| 4,615,993 | 10/1986 | Schirrmacher et al. | 502/55 |
| 4,663,493 | 5/1987 | Vora et al. | 585/656 |
| 4,874,505 | 10/1989 | Bartilucci et al. | 208/131 |
| 4,922,048 | 5/1990 | Harandi | 585/310 |
| 4,922,051 | 5/1990 | Nemet-Mavrodin et al. | 585/418 |

OTHER PUBLICATIONS

Hydrocarbon Processing, vol. 60, No. 9, Sep. 1981, pp. 134–138.
"Alkane Dehydrogenation by Iridium Complexes" J. Am. Chem. Soc., vol. 104, 107 (1982) R. Crabtree et al.
"Reaction of C—H Bonds in Alkanes with Bis(diphosphine) Complexes of Iron" J. Am. Chem. Soc., vol. 109, 2825 (1987).
"The Selective Conversion of n-Pentane into Pent-1-ene via Trihydrido (trans-penta-1,3-diene)bis(triarylphosphine)rhenium", J. Chem. Soc. Comm 1235 (1982).
Zeolite Chemistry and Catalysis 771 (ACS Monograph 171, 1976) A. P. Bolton.
Hydrogen Processing, vol. 61, No. 5, May 1982, pp. 110–112.
J. Am. Chem. Soc. vol. 108, 1606 (1986).

Primary Examiner—Anthony McFarlane
Assistant Examiner—Nhat D. Phan
Attorney, Agent, or Firm—Alexander J. McKillop; Dennis P. Santini; Robert B. Furr, Jr.

[57] ABSTRACT

The present invention provides a process for producing a selected paraffin from a reaction mixture containing
(i) an acceptor olefin having the carbon backbone structure of said selected paraffin;
(ii) a donor paraffin having a carbon backbone structure different from that of said selected paraffin;
(iii) less than about 10 mole percent molecular hydrogen; which process comprises the steps of contacting said reaction mixture with a heterogeneous catalyst comprising active carbon in the absence of an added catalytic metal or metal compound to convert at least a portion of said acceptor olefin to said selected paraffin and to dehydrogenate at least a portion of said donor paraffin.

18 Claims, No Drawings

OTHER PUBLICATIONS

"New Process Produces Low-Pour Oils" R. N. Bennett et al. *The Oil and Gas Journal,* Jan. 6, 1975, pp. 69-73.

"Activation of C—H Bonds in Saturated Hydrocarbons, The Selective Catalytic Functionalisation of Methyl Groups by Means of a Soluble Iridium Polyhydride System" 16 *Tetrahedron Letters* 1999 (1985), H. Felkin et al.

"Iridium Pentahydride Complex Catalyzed Formation of C—C bond by C—H Bond Activation Followed By Olefin Insertion" Tetrahedron Letters 28, 3249 (1987), Y. Lin et al.

*Handbook of Petroleum Refining Processes* 23-28 (R. A. Meyers, ed., 1986).

"Alkylation of Isobutane with $C_4$ Olefins", L. F. Albright et al., *Ind. Eng. Chem. Res.,* vol. 27, 381-397 (1988).

"The Activation of C—H Bonds in Cyclopentane by Bis(phosphine)rhenium Heptahydrides", D. Baudry et al., *J. Chem. Soc. Comm.* 1234 (1980).

PROCESS FOR HYDROGENATING ALKENES IN THE PRESENCE OF ALKANES AND A HETEROGENEOUS CATALYST

FIELD OF THE INVENTION

The present invention relates to a process for producing more highly saturated hydrocarbon streams from less highly saturated hydrocarbon feedstreams. Particularly, the invention relates to a process for hydrogenating an alkene in the presence of an alkane and in the absence of intentionally added molecular hydrogen.

BACKGROUND OF THE INVENTION

Recent regulatory developments have led refiners to seek methods for reformulating motor gasolines to meet increasingly stringent air quality requirements. These techniques include reducing the olefin and aromatic content of the motor gasoline while maintaining the desired octane rating by increasing the relative content of isooctane (trimethylpentane) and other octane-enhancing additives such as oxygenates.

Commercial isobutane:butene alkylation, catalyzed by a strong mineral acid such as HF or $H_2SO_4$, produces a highly desirable motor gasoline blending component which is enriched in high-octane trimethylpentane. Thus with the advent of more restrictive air quality regulations, the known commercial isobutane:butene alkylation processes present a seemingly ideal solution to the problem of reformulating motor gasoline to minimize both evaporative losses from storage as well as pollutants emissions from gasoline engine operations.

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used large volumes of liquid Bronsted acid catalysts such as hydrofluoric or sulfuric acid under relatively low temperature conditions. Acid strength is preferably maintained at 88 to 94 weight percent by the continuous addition of fresh acid and the continuous withdrawal of spent acid. Liquid acid catalyzed isoparaffin:olefin alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381-397, (1988). For a survey of hydrofluoric acid catalyzed alkylation, see 1 *Handbook of Petroleum Refining Processes* 23-28 (R. A. Meyers, ed., 1986).

Both sulfuric acid and hydrofluoric acid alkylation share inherent drawbacks including environmental and safety concerns, acid consumption, and sludge disposal. Research efforts have been directed to developing alkylation catalysts which are equally as effective as sulfuric or hydrofluoric acids but which avoid many of the problems associated with these two acids, and alternatives such as Lewis acids, e.g., $BF_3$, have been explored. While Lewis acids generally pose fewer and less severe safety and environmental concerns than strong liquid acids such as HF and $H_2SO_4$, it would be desirable to produce paraffin-rich product streams useful as gasoline blending components without the use of noxious and/or corrosive liquid catalyst systems.

The typical petroleum refinery generates numerous olefinic streams, which, upon hydrogenation and optional fractionation, would be useful gasoline blending components. Examples of such streams include the olefinic gasoline and naphtha byproducts of catalytic hydrodewaxing processes such as the MLDW (Mobil Lubricant Dewaxing) and MDDW (Mobil Distillate Dewaxing). Additional examples include olefinic gasoline cuts from delayed coking units (thermally cracked gasoline), as well as from catalytic cracking process units such as a Fluidized Catalytic Cracking (FCC) process. Lighter olefins may be easily dimerized or oligomerized to provide suitable feedstocks, for example in a process such as MOGD/MOGDL (Mobil Olefins to Gasoline and Distillate/ Mobil Olefins to Gasoline, Distillate and Lube Stock), or MOCI (Mobil Olefins to Chemical Intermediates). Examples of processes which product olefinic stocks include the processes taught in U.S. Pat. Nos. 4,922,048 to Harandi and 4,922,051 to Nemet-Mavrodin et al. Additional examples of light olefin dimerization/oligomerization processes include Dimersol (light olefin dimerization), Isopol (selective isobutene isomerization) and Selectopol (selective butadiene polymerization). See *Hydrocarbon Processing*, Vol. 61, No. 5, May 1982, pp. 110-112, and *Hydrocarbon Processing*, Vol. 60, No. 9, Sep. 1981, pp. 134-138.

Previously known techniques for hydrogenating olefinic streams required contacting the olefinic stream with molecular hydrogen in the presence of a hydrogenation catalyst at elevated temperature and pressure, for example in the pretreater section of a catalytic reforming process unit. But it is well known that catalytic hydrogenation in the presence of molecular hydrogen poses its own set of safety and environmental concerns, and requires an expensive supply of hydrogen-rich feed gas.

Hydrogenation of selected less highly saturated hydrocarbons by hydrogen transfer from a more highly saturated hydrocarbon has been explored with homogeneous catalyst systems. See for example, D. Baudry, M. Ephritikhine and H. Felkin "The Activation of C—H Bonds in Cyclopentane by Bis(phosphine)rhenium Heptahydrides" *J. Chem. Soc. Comm.* 1243 (1980), H. Felkin, T. Fillebeen-Khan, R. Holmes-Smith and L. Yingrui "Activation of C—H Bonds in Saturated Hydrocarbons, The Selective Catalytic Functionalisation of Methyl Groups by Means of a Soluble Iridium Polyhydride System" 16 *Tetrahedron Letters* 1999 (1985), Y. Lin, D. Ma and X. Lu "Iridium Pentahydride Complex Catalyzed Formation of C—C Bond by C—H Bond Activation Followed by Olefin Insertion" 28 *Tetrahedron Letters* 3249 (1987), R. Crabtree, M. Melles, J. Mihelcic and J. Quirk "Alkane Dehydrogenation by Iridium Complexes" 104 *J. Am. Chem. Soc.* 107 (1982), D. Baudry, M. Ephritikhine, H. Felkin and J. Zakrewski "The Selective Conversion of n-Pentane into Pent-1-ene via Trihydrido(trans-penta-1,3-diene)bis(triarylphosphine)rhenium" *J. Chem. Soc. Comm.* 1235 (1982), and M. Baker and L. Field "Reaction of C—H Bonds in Alkanes with Bis(diphosphine) Complexes of Iron" 109 *J. Am. Chem. Soc.* 2825 (1987). However, these homogeneous catalysts have been found to be unsuitable for industrial application due to several factors, including the inherent difficulties in separating the homogeneous catalyst from the reaction products. Research in the area of hydrogen-deuterium exchange of alkanes over supported metal catalysts has also been disclosed in 108 J. Am. Chem. Soc. 1606 (1986). Alkylation reactions in the presence of solid acid catalysts have also been explored. See A. P. Bolton, *Zeolite Chemistry and Catalysis* 771 (ACS Monograph 171, 1976).

SUMMARY OF THE INVENTION

The present invention provides a process for hydrogenating an alkene in the presence of an alkane over a heterogeneous catalyst. The invention further provides a process for hydrogenating an alkene in the presence of an alkane wherein the reaction mixture contains less than about 10 mole percent hydrogen, preferably in the absence of intentionally added molecular hydrogen, comprising contacting a mixture of the alkene and the alkane with a heterogeneous catalyst comprising active carbon, for example, active carbon derived from peat, from thermal treatment of petroleum fractions, or from a synthetic source. The most preferred active carbon catalyst has been found to be provide commercially useful selectivity and yield in the absence of added metal.

The invention further provides a process for producing a selected paraffin from a reaction mixture containing (i) an acceptor olefin having the carbon backbone structure of said selected paraffin;

(ii) a donor paraffin having a carbon backbone structure different from that of said selected paraffin;

(iii) less than 10 mole percent molecular hydrogen; which process comprises contacting said reaction mixture with a heterogeneous catalyst comprising porous carbon to convert at least a portion of said acceptor olefin to said selected paraffin and to dehydrogenate at least a portion of said donor paraffin.

The acceptor olefin and donor paraffin may be any suitable pair. Isoparaffins are preferred donor paraffins, and isobutane is particularly preferred. $C_5$–$C_8$ olefins are preferred acceptor olefins, with isooctene being particularly preferred for the production of an isooctane-containing motor gasoline blending component.

The process of the invention typically yields, in addition to the selected paraffin, side products such as cracked and/or oligomerized aliphatics and aromatics may be formed. Process conditions, however, are preferably controlled to minimize formation of such side products. Generally, high temperatures, low pressures, and short contact times (within the disclosed ranges) favor cracked side products while, in contrast, low temperatures, high pressures, and relatively long contact times (within the disclosed ranges) favor the formation of oligomerized side products. Aromatization of side products may also occur at elevated temperatures with relatively long contact times.

DETAILED DESCRIPTION

Feedstocks

Olefinic feedstocks suitable for use in the present invention include numerous olefinic streams produced by petroleum refining operations, for example, a cracked olefinic stream such as an olefinic gasoline boiling range fraction from a delayed coker process unit. Delayed coking processes are taught in U.S. Pat. No. 3,917,564 to Meyers and U.S. Pat. No. 4,874,505 to Bartilucci et al., both of which patents are incorporated herein by reference.

Suitable olefinic feedstocks are also produced as by-products in catalytic dewaxing processes, as described in U.S. Pat. No. 4,922,048, which patent is incorporated herein by reference.

Catalytic dewaxing of hydrocarbon oils to reduce the temperature at which precipitation of waxy hydrocarbons occurs is a known process and is described, for example, in the Oil and Gas Journal, Jan. 6, 1975, pages 69–73. A number of patents have also described catalytic dewaxing processes. For example, U.S. Pat. RE. No. 28,398 describes a process for catalytic dewaxing with a catalyst comprising a medium-pore zeolite and a hydrogenation/dehydrogenation component. U.S. Pat. No. 3,956,102 describes a process for hydrodewaxing a gas oil with a medium-pore zeolite catalyst. U.S. Pat. No. 4,100,056 describes a Mordenite catalyst containing a Group VI or a Group VIII metal which may be used to dewax a distillate derived from a waxy crude. U.S. Pat. No. 3,755,138 describes a process for mild solvent dewaxing to remove high quality wax from a lube stock, which is then catalytically dewaxed to specification pour point. Such developments in catalytic dewaxing have led to the MLDW (Mobil Lube Dewaxing) and MDDW (Mobil Distillate Dewaxing) process.

Catalytic dewaxing processes may be followed by other processing steps such as hydrodesulfurization and denitrogenation in order to improve the qualities of the product. For example, U.S. Pat. No. 3,668,113 describes a catalytic dewaxing process employing a Mordenite dewaxing catalyst which is followed by a catalytic hydrodesulfurization step over an alumina-based catalyst. U.S. Pat. No. 4,400,265 describes a catalytic dewaxing/hydrodewaxing process using a zeolite catalyst having the structure of ZSM-5 wherein gas oil is catalytically dewaxed followed by hydrodesulfurization in a cascade system. The foregoing dewaxing processes exemplify low-severity medium-pore catalyzed dewaxing processes which produce a low octane naphtha by-product. Another example of a low severity medium-pore catalyzed conversion reaction is olefin oligomerization.

Recent developments in zeolite catalysts and hydrocarbon conversion methods and apparatuses have created interest in utilizing olefinic feedstocks for producing heavier hydrocarbons, such as $C_5+$ gasoline, distillate or lubes. These developments form the basis of the Mobil olefins to gasoline/distillate (MOGD) method and apparatus, and the Mobil olefins to gasoline/distillate/lubes (MOGDL) method and apparatus.

In MOGD and MOGDL, olefins are catalytically converted to heavier hydrocarbons by catalytic oligomerization using an acid crystalline zeolite, such as a zeolite catalyst having the structure of ZSM-5. Process conditions can be varied to favor the formation of either gasoline, distillate or lube range products. U.S. Pat. Nos. 3,960,978 and 4,021,502 to Plank et al. disclose the conversion of $C_2$–$C_5$ olefins alone or in combination with paraffinic components, into higher hydrocarbons over a crystalline zeolite catalyst. U.S. Pat. Nos. 4,150,062; 4,211,640 and 4,227,992 to Garwood et al. have contributed improved processing techniques to the MOGD system. U.S. Pat. No. 4,456,781 to Marsh et al. has also disclosed improved processing techniques for the MOGD system.

U.S. Pat. Nos. 4,422,185 and 4,483,760 to Tabak disclose two-stage catalytic processes for upgrading hydrocarbon feedstocks, the texts of which are incorporated by reference as if set forth at length herein.

The '185 patent to Tabak teaches a process for converting an olefinic feedstock containing ethene and heavier alkenes to a product rich in distillate and olefinic gasoline. Effluent from a first stage distillate mode reactor is flashed to separate an ethylene-rich product stream which is then charged to a second stage gasoline mode reactor. A disadvantage of the process taught by '185 is that the highly olefinic gasoline product stream is of a relatively low octane and reduces the gasoline pool octane.

The '760 patent to Tabak teaches a process for catalytically dewaxing a middle distillate separating an olefinic by-product from the dewaxed distillate product stream, and upgrading a gasoline fraction at temperatures above 900° F. In addition, the second catalytic reactor is operated to convert at least 10 wt. % of the olefinic by-product fraction to fuel oil (material boiling above 380° F.).

Olefinic feedstocks may be obtained from various sources, including from fossil fuel processing streams such as gas separation units, from the cracking of $C_2$-hydrocarbons, such as LPG (liquified petroleum gas) from coal by-products, from various synthetic fuel processing streams, and as by-products from fluid catalytic cracking (FCC) and thermal catalytic cracking (TCC) process units. U.S. Pat. No. 4,100,218 to Chen et al. teaches thermal cracking of ethane to ethylene, with subsequent conversion of ethylene to LPG and gasoline over a zeolite catalyst having the structure of ZSM-5.

The conversion of olefins in an MOGDL system may occur in a gasoline mode, the olefins are typically oligomerized at temperatures ranging from 400° to 800° F. and pressures ranging form 10 to 1000 psig. The distillate/lube mode, olefins are catalytically oligomerized to distillate at temperature ranging from 350° F. to 600° F. and pressures ranging from 100 to 3000 psig. The distillate is then upgraded by hydrotreating and separating the hydrotreated distillate to recover lubes.

These low severity catalytic hydrocarbon conversion processes typically produce a highly olefinic gasoline stream having a motor clear octane number in the range of 76 to 81. The product stream's low octane number makes it unsuitable for use as a gasoline blending component.

Catalytic reforming is widely used to increase octane in gasoline boiling range feedstocks. The nature of the reforming reaction is such that a paraffinic feedstock is preferred over an olefinic feedstock. Olefinic feedstocks tend to form excessive amounts of coke in the reformer reactors and cause more rapid deactivation of the reforming catalyst. Consequently, reformers are typically equipped with pretreaters which catalytically react naphtha with hydrogen to remove sulfur compounds and to saturate olefins. Sulfur compounds are catalyst poisons and are removed from the process stream by catalytic addition of hydrogen to for $H_2S$. Hydrogen consumption is related to the concentration of olefinic compounds in pretreater feed and olefinic feeds, therefore, consume more hydrogen during pretreatment than paraffinic feeds, making olefinic feeds more costly to pretreat.

U.S. Pat. No. 3,890,218 to Morrison teaches a reforming process using a crystalline zeolite catalyst having the structure of ZSM-5. The Morrison patent shows a plot of $C_5+$ volume percent recovery as a function of research clear octane number for a given feed and process conditions. For a general discussion of naphtha reforming, see 17 Kirk Othmer Encyclopedia of Chemical Technology, 218-220, 3rd edition, 1982.

The metallic components useful as catalyst components in the process of the present invention include the metals (as well as the metallic oxides and sulfides) of Group VIII of the Periodic Table of the Elements, which Table is shown at the back inside cover of F. A. Cotton and G. Wilkinson *Advanced Inorganic Chemistry A Comprehensive Text*, John Wiley and Sons, 1980. Platinum, iridium, nickel, and palladium (as well as the oxides and sulfides thereof) are preferred, and palladium is particularly preferred.

Both inert and catalytically active supports may be employed, with examples including one or more of alumina, silica, silica-alumina, zeolites, clays, Kieselguhr, titania, magnesia and active carbons from sources such as coal, coke, and coconut shell. Supports such as active carbon, alumina, silica, and silica-alumina are preferred, with active carbon being most preferred. Active carbon is useful in the present invention in the presence or absence of added catalytic metal, and may be activated and/or regenerated by selective oxidation with air or peroxides, fluorine, or sulfur oxides. Activation may also be effected by treatment with caustic, fluorine compounds such as HF and CsF, phosphoric acid, sulfuric acid, zinc chloride, potassium sulfide, and/or steam. Hydrogen, carbon oxides, or mixtures thereof, may also be used for activation.

The Group VIII metals may also be exchanged onto zeolites to provide a zeolite catalyst having dehydrogenation activity. Metals may also be added to the zeolite by impregnation, mulling, mixing, coprecipitation, or a combination of one or more of these techniques.

Solid supports useful in the present invention include both zeolitic and nonzeolitic solids having relatively low acid activity. Useful nonzeolitic solids may be selected from among the diverse inorganic oxides, examples of which include, but are not limited to, silica, alumina, boria, oxides of phosphorus, titanium dioxide, zirconium dioxide, chromia, zinc oxide, magnesia, calcium oxide, alumina-magnesia, alumina-zirconia, as well as the naturally occurring inorganic oxides of various states of purity such as bauxite, clay, diatomaceous earth, merely to name a few.

The large pore crystalline molecular sieves which can be used in the present invention include those which absorb 2,2,4-trimethylpentane. Representative large pore crystalline molecular sieves include, for example, the following zeolites: ZSM-3, ZSM-4, ZSM-12, ZSM-18, ZSM-20, zeolite L, mordenite, faujasite, zeolite Y, and the rare earth metal-containing forms of the above-listed zeolites. Zeolite Beta can also be used in the present invention, although it is understood that zeolite Beta may exhibit characteristics of a medium-pore zeolite or a large-pore zeolite depending upon process conditions.

Zeolites having an effective pore size of generally from about 5 to about 8 Angstroms, such as to freely sorb normal hexane, are also useful support materials in the process of the invention. A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732 discloses Constraint Index values for typical zeolite materials and is incorporated by reference as if set forth at length herein.

Catalysts comprising a zeolite having a Constraint Index of between about 1 and about 12. Examples of such zeolite catalysts include ZSM-5, ZSM-11, ZSM-12, ZSM-22, ZSM-23, ZSM-35 and ZSM-48.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous ZSM-5); 4,100,262 and 4,139,600, the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference. ZSM-48 and the conventional preparation thereof is taught by U.S. Pat. No. 4,375,573, the disclosure of which is incorporated herein by reference.

Gallium-containing zeolite catalysts are useful in the present invention and are disclosed in U.S. Pat. No. 4,350,835 and U.S. Pat. No. 4,686,312, both of which are incorporated by reference as if set forth at length herein.

Zinc-containing zeolite catalysts are useful in the present invention, for example, U.S. Pat. No. 4,392,989 and U.S. Pat. No. 4,472,535, both of which are incorporated by reference as if set forth at length herein.

Catalysts such as ZSM-5 combined with a Group VIII metal described in U.S. Pat. No. 3,856,872, incorporated by reference as if set forth at length herein, are also useful in the present invention.

Zeolite MCM-22 is also a useful catalytic material in accordance with the present invention. U.S. Pat. No. 4,954,325 teaches the synthesis of MCM-22, and is incorporated by reference as if set forth at length herein.

The medium- or large-pore zeolite selected for use in the present alkylation process generally exhibits a relatively low Alpha value, preferably less than about 200, more preferably less than about 50, most preferably less than about 1.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec$^{-1}$). The Alpha Test is described in U.S. Pat. No. 3,354,078; in the *Journal of Catalysis*, Vol. 4., p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395. The foregoing references are incorporated by reference as if set forth at length herein for description of the Alpha Value test.

Zeolites of low acidity, i.e. zeolites having alpha values of less than about 200, can be achieved by a variety of techniques including (a) synthesizing a zeolite with a high silica:alumina ratio, (b) steaming, (c) steaming followed by dealuminization, and (d) substituting framework aluminum with other species. For example, in the case of steaming, the zeolite can be exposed to steam at elevated temperatures ranging from about 500° to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures using elevated pressure, e.g. at from about 350° to about 750° F. with pressure of from about 10 to about 200 atmospheres. Specific details of several steaming procedures may are disclosed in U.S. Pat. Nos. 4,325,994; 4,374,296; and 4,418,235, which patents are incorporated as if set forth at length herein. In addition to, or apart from these steaming procedures, the surface acidity of the zeolite can be eliminated or reduced by treatment with bulky reagents as described in U.S. Pat. No. 4,520,221, which patent is incorporated herein by reference. Finally, the acidity of the zeolite may also be reduced by high temperature calcination in the absence of steam as taught in U.S. Pat. Nos. 4,724,270 and 4,783,571 to Chang, Hellring, and Socha, which patents are incorporated by reference as if set forth at length herein.

Additional molecular sieves which find utility in conjunction with the present invention include pillared silicates and/or clays; aluminophosphates, e.g. ALPO-5, VPI-5; silicoaluminophosphates, e.g. SAPO-5, SAPO-37, SAPO-31, SAPO-40, SAPO-41; and other metal aluminophosphates. These are variously described in U.S. Pat. Nos. 4,440,871; 4,554,143; 4,567,029; 4,666,875; and 4,742,033.

Process Conditions

The process of the present invention proceeds under relatively mild conditions of temperature, pressure, and liquid hourly space velocity (LHSV). Higher temperatures and pressures within the ranges disclosed below in Table I are generally preferred, with temperatures of around 400° C. being particularly preferred when the catalyst comprises active carbon.

TABLE 1

| | Broad Range | Preferred Range |
|---|---|---|
| Temperature | 100–600° C. | 350–450° C. |
| Pressure | 0–3000 psig | 0–2000 psia |
| LHSV | 0–20 hr$^{-1}$ | 0.1–5.0 Ohr$^{-1}$ |
| Olefin:Paraffin Weight Ratio in Feedstock | 1:100 to 1:1 | 1:50 to 1:2 |

EXAMPLES

Examples 1 and 2

Palladium on activated carbon (obtained from Johnson-Mathey, Alfa Products catalog number 31961, lot #H18H, 6–8 mesh pellets) was tested (4 ml, 1.393 g., 14/20 mesh) in a fixed-bed unit using a ⅜" stainless steel reactor. Catalyst was reduced with hydrogen at 350° C. and 300 psig, and the reactor was then vented to atmospheric pressure prior to introduction of feed. The feed was prepared from commercial sources without purification, and metered as a 15-17 weight percent solution of 2,2,4-trimethylpentenes (99 weight percent 2,2,4-trimethylpentenes obtained from Aldrich, 1001 West Saint Paul Avenue, Milwaukee, Wisc., 53233) in isobutane (isobutane obtained from Matheson Chemical Company, Bridgeport, N.J.) via a syringe pump. Reaction pressure was regained from added feed. Total effluent was collected under pressure as a liquid and sampled off-line using a high pressure syringe. A 16 hour pre-run was conducted which included reactor filling and collection of 25.58 grams of effluent before starting the first material balance. Samples were analyzed by gas chromatograph through a 60 meter DB-1 capillary column after injection with a high pressure syringe.

Feed and reactor effluent data in Examples 1-15 were normalized to exclude isobutane, which was used in large excess 2,2,4-Trimethylpentene-1 and 2,2,4-trimethylpentene-2 were summed as 2,2,4-trimethylpentenes feed. Results for LHSV varying from 1 to 0.5 are shown in Table 2. Conversion of 2,2,4-trimethylpentenes increased roughly 70% from 4% to 7% when contact time was doubled.

TABLE 2

| Normalized Components (wt %) | FEED | EXAMPLE 1 | EXAMPLE 2 |
| --- | --- | --- | --- |
| $C_1$-$C_3$ | 0.35 | 0.35 | 0.31 |
| n-Butane | 0.40 | 0.46 | 0.39 |
| Isobutene | 0.00 | 1.51 | 3.02 |
| 2-Butenes | 0.00 | 0.00 | 0.00 |
| $C_5$-$C_7$ | 0.10 | 0.22 | 0.11 |
| 2,2,4-Trimethylpentane | 0.00 | 1.70 | 3.35 |
| 2,4,4-Trimethylpentenes | 98.62 | 94.53 | 91.53 |
| Other C8's | 0.54 | 1.23 | 1.30 |
| C9+ | 0.00 | 0.00 | 0.00 |
| 2,2,4-Trimethylpentane in C8 Product (%) | | 70.84 | 81.48 |
| C8-product/Isobutene (wt) | | 1.59 | 1.36 |
| 2,4,4-Trimethylpentenes conversion (%) | | 4.15 | 7.19 |
| Flow Rate (LHSV) | | 1.0 | 0.5 |
| Reactor Temperature (C.) | | 300 | 300 |
| Reactor Pressure (psig) | | 250 | 350 |

The procedure of Examples 1 and 2 was repeated with 1 weight percent palladium on alumina (Examples 3-5, Table 3), 5 weight percent palladium on zeolite Beta (Examples 6-8, Table 4), 5 weight percent palladium on cation-exchanged zeolite Beta (Examples 9 and 10, Table 5), 55-60 weight percent nickel on kieselguhr (Examples 11 and 12, Table 6), and 5 weight percent iridium on cation-exchanged alumina (Examples 13-15, Table 7).

TABLE 3

| Normalized Components (wt %) | EXAMPLE 3 | EXAMPLE 4 | EXAMPLE 5 |
| --- | --- | --- | --- |
| $C_1$-$C_3$ | 0.76 | 0.70 | 0.23 |
| n-Butane | 0.10 | 0.10 | 0.33 |
| Isobutene | 7.54 | 7.16 | 1.12 |
| 2-Butenes | 0.00 | 0.00 | 0.00 |
| $C_5$-$C_7$ | 0.17 | 0.16 | 0.14 |
| 2,2,4-Trimethylpentane | 3.35 | 3.41 | 1.89 |
| 2,4,4-Trimethylpentenes | 85.72 | 86.17 | 95.45 |
| Other C8's | 2.36 | 2.31 | 0.84 |
| C9+ | 0.00 | 0.00 | 0.00 |
| 2,2,4-Trimethylpentane in C8 Product (%) | 64.76 | 65.79 | 85.97 |
| C8-product/Isobutene (wt) | 0.69 | 0.72 | 1.95 |
| 2,4,4-Trimethylpentenes conversion (%) | 13.08 | 12.62 | 3.21 |
| Flow Rate (LHSV) | 1.0 | 1.0 | 1.0 |
| Reactor Temperature (C.) | 350 | 350 | 300 |
| Reactor Pressure (psig) | 250 | 250 | 250 |

TABLE 4

| Normalized Components (wt %) | EXAMPLE 6 | EXAMPLE 7 | EXAMPLE 8 |
| --- | --- | --- | --- |
| $C_1$-$C_3$ | 1.10 | 0.53 | 0.37 |
| n-Butane | 0.18 | 0.13 | 0.19 |
| Isobutene | 37.04 | 29.76 | 7.45 |
| 2-Butenes | 4.19 | 2.04 | 0.66 |
| $C_5$-$C_7$ | 16.26 | 6.31 | 0.97 |
| 2,2,4-Trimethylpentane | 0.39 | 0.20 | 0.26 |
| 2,4,4-Trimethylpentenes | 1.31 | 4.75 | 66.39 |
| Other C8's | 26.59 | 52.41 | 22.79 |
| C9+ | 12.94 | 3.88 | 0.91 |
| 2,2,4-Trimethylpentane in C8 Product (%) | 1.46 | 0.38 | 1.17 |
| C8-product/Isobutene (wt) | 0.71 | 1.75 | 3.02 |
| 2,4,4-Trimethylpentenes conversion (%) | 98.68 | 12.62 | 3.21 |
| Flow Rate (LHSV) | 1.0 | 1.0 | 1.0 |
| Reactor Temperature (C.) | 300 | 250 | 100 |
| Reactor Pressure (psig) | 250 | 250 | 250 |

TABLE 5

| Normalized Components (wt %) | EXAMPLE 9 | EXAMPLE 10 |
| --- | --- | --- |
| $C_1$-$C_3$ | 0.24 | 0.38 |
| n-Butane | 0.50 | 0.54 |
| Isobutene | 9.12 | 11.77 |
| 2-Butenes | 0.24 | 0.00 |
| $C_5$-$C_7$ | 1.08 | 1.18 |
| 2,2,4,-Trimethylpentane | 0.22 | 0.51 |
| 2,4,4-Trimethylpentenes | 56.62 | 59.03 |
| Other C8's | 31.31 | 26.59 |
| C9+ | 0.68 | 0.00 |
| 2,2,4-Trimethylpentane in C8 Product (%) | 0.71 | 1.91 |
| C8-product/Isobutene (wt) | 3.40 | 2.26 |
| 2,4,4-Trimethylpentenes conversion (%) | 42.58 | 40.14 |
| Exchange Cation | Ce | Ba |
| Flow Rate (LHSV) | 1.0 | 1.0 |
| Reactor Temperature (C.) | 200 | 100 |
| Reactor Pressure (psig) | 250 | 300 |

TABLE 6

| Normalized Components (wt %) | EXAMPLE 11 | EXAMPLE 12 |
| --- | --- | --- |
| $C_1$-$C_3$ | 12.24 | 0.41 |
| n-Butane | 1.11 | 0.48 |
| Isobutene | 15.18 | 2.55 |
| 2-Butenes | 1.05 | 0.00 |
| $C_5$-$C_7$ | 6.61 | 1.66 |
| 2,2,4-Trimethylpentane | 3.15 | 1.60 |
| 2,4,4-Trimethylpentenes | 47.99 | 90.76 |
| Other C8's | 10.39 | 1.96 |
| C9+ | 2.28 | 0.57 |
| 2,2,4-Trimethylpentane in C8 Product (%) | 24.26 | 52.83 |

TABLE 6-continued

| Normalized Components (wt %) | EXAMPLE 11 | EXAMPLE 12 |
|---|---|---|
| C8-product/Isobutene (wt) | 0.86 | 1.19 |
| 2,4,4-Trimethylpentenes conversion (%) | 51.33 | 7.96 |
| Added Sodium wt % | — | 0.50 |
| Flow Rate (LHSV) | 1.0 | 1.0 |
| Reactor Temperature (C.) | 250 | 250 |
| Reactor Pressure (psig) | 300 | 300 |

TABLE 7

| Normalized Components (wt %) | EXAMPLE 13 | EXAMPLE 14 | EXAMPLE 15 |
|---|---|---|---|
| $C_1$-$C_3$ | 1.17 | 0.33 | 0.45 |
| n-Butane | 0.59 | 0.42 | 0.48 |
| Isobutene | 55.27 | 14.32 | 39.96 |
| 2-Butenes | 1.73 | 0.00 | 0.00 |
| $C_5$-$C_7$ | 2.97 | 0.13 | 0.11 |
| 2,2,4-Trimethylpentane | 0.25 | 0.00 | 0.24 |
| 2,4,4-Trimethylpentenes | 7.96 | 79.33 | 47.68 |
| Other C8's | 28.24 | 5.30 | 10.23 |
| C9+ | 1.82 | 0.17 | 0.84 |
| 2,2,4-Trimethylpentane in C8 Product (%) | 0.88 | 0.00 | 2.24 |
| C8-product/Isobutene (wt) | 0.51 | 0.33 | 0.25 |
| 2,4,4-Trimethylpentenes conversion (%) | 91.93 | 19.55 | 51.65 |
| Exchange Cation wt % | 1% Ba | 1% Ba | 0.5% Na |
| Flow Rate (LHSV) | 1.0 | 8.0 | 1.0 |
| Reactor Temperature (C.) | 300 | 300 | 250 |
| Reactor Pressure (psig) | 300 | 300 | 300 |

EXAMPLES 16-19

In Examples 16-19, activated carbon Norit PK1-3 (8/20 mesh) was used as received from American Norit Company (1050 Crown Point Parkway, Suite 1500 Atlanta, Ga. 30338). The catalyst (4 ml) was preheated in flowing helium to reaction temperature, then pretreated with isobutane (obtained from Matheson Chemical Company) for several hours (0.962 LHSV) before introducing octene-1 (obtained from the Aldrich Company) from a separate pump (0.038 LHSV). The reaction was compared at 80 and 800 psig, at both 300° and 400° C. The entire reactor effluent was collected as a liquid under pressure and analyzed by GC using a high pressure syringe for sample transfer. Techniques including GC/MS, bromination/GC, and comparison with available standards were used to identify the reaction products. Results for Examples 16-19 are shown below in Table 8.

TABLE 8

Conversion of Isobutane/Octene-1 Over Activated Carbon
Data shows conversion increases at higher pressures and temperatures

| | Ex. 16 | Ex. 17 | Ex.18 | Ex. 19 |
|---|---|---|---|---|
| Temperature (C.) | 300 | 300 | 400 | 400 |
| Pressure (psig) | 80 | 800 | 80 | 800 |
| Hours on Olefin | 40.25 | 70.75 | 127.25 | 94.75 |
| Isobutane/C8 = (molar) | 91 | 132 | 141 | 104 |
| Normalized Products (wt %) | | | | |
| IC4= | 2.67 | 7.37 | 20.46 | 24.42 |
| C5's | 0.00 | 0.00 | 0.89 | 0.82 |

TABLE 8-continued

Conversion of Isobutane/Octene-1 Over Activated Carbon
Data shows conversion increases at higher pressures and temperatures

| | Ex. 16 | Ex. 17 | Ex.18 | Ex. 19 |
|---|---|---|---|---|
| C6's | 4.20 | 5.09 | 2.35 | 1.81 |
| 2,2,4-Trimethylpentanes | 1.21 | 1.30 | 0.85 | 1.09 |
| C7's | 0.00 | 0.00 | 0.42 | 0.00 |
| 2,4,4-Trimethylpentenes | 22.23 | 25.56 | 0.55 | 0.00 |
| Me-C7's and DMH's | 0.45 | 0.00 | 1.24 | 1.17 |
| n-Octane | 58.83 | 56.19 | 65.93 | 64.15 |
| Methyloctanes | 2.39 | 0.00 | 0.34 | 0.00 |
| Ethylbenzene | 2.45 | 1.54 | 2.87 | 2.45 |
| Meta-&Para-Xylene | 0.41 | 0.00 | 0.19 | 0.00 |
| Ortho-Xylene | 5.16 | 2.95 | 3.90 | 4.10 |
| TOTAL | 100.00 | 100.00 | 100.00 | 100.00 |
| Conversions | | | | |
| Total C8-olefin | 24.73 | 19.06 | 81.81 | 94.94 |
| Isobutane | 0.19 | 0.15 | 0.33 | 0.63 |
| C8-Olefin Product Selectivities | | | | |
| C8-paraffin | 78.42 | 82.92 | 86.04 | 87.37 |
| Aromatics | 11.40 | 7.13 | 9.58 | 9.42 |
| Other C5-plus | 10.18 | 9.95 | 4.38 | 3.20 |
| Isobutane Product Selectivities | | | | |
| Isobutylene | 10.24 | 21.56 | 93.64 | 95.81 |
| 2,4,4-Trimethylpentene | 85.21 | 74.71 | 2.52 | 0.00 |
| 2,2,4-Trimethylpentane | 4.55 | 3.74 | 3.84 | 4.19 |
| H2 Sources | | | | |
| % H2 balance | −7.3 | −15.9 | 8.5 | −0.7 |
| % Isobutylene Dehydrogenation | 67.3 | 82.8 | 66.5 | 71.1 |
| % Aromatization | 32.7 | 17.2 | 33.5 | 28.9 |

EXAMPLES 20-23

For Examples 20-23, activated carbon Norit PK1-3 (8/20 mesh, 4 ml) was preheated in helium and pretreated with isobutane for several hours (0.962 LHSV) before introducing 2,3,4-trimethylpentene (Wiley) from a separate pump (0.038 LHSV). The reaction was carried out at 400° C. and 800 psig. The entire reactor effluent was collected as a liquid under pressure and analyzed by GC using a high pressure syringe for sample transfer. Techniques including GC/MS, bromination/GC, and comparison with available standards were used to identify the reaction products.

TABLE 9

Conversion of Isobutane/2,3,4-Trimethylpentene Over Activated Carbon

| | Ex. 20 | Ex. 21 | Ex. 22 | Ex. 23 |
|---|---|---|---|---|
| Normalized Products | | | | |
| C3 | 11.79 | 12.70 | 10.02 | 9.75 |
| Isobutylene | 26.67 | 26.76 | 20.72 | 21.30 |
| Isopentane | 8.14 | 7.10 | 5.30 | 5.11 |
| Other C5 | 8.79 | 9.05 | 9.03 | 8.19 |
| C6 | 0.59 | 0.00 | 0.53 | 0.00 |
| C7 | 0.56 | 0.00 | 0.35 | 0.00 |
| 2,3,4-Trimethylpentane | 24.79 | 21.59 | 18.43 | 18.36 |
| 2,3,4-Trimethylpentene | 10.22 | 14.29 | 21.17 | 23.11 |
| Other C8 | 8.45 | 8.51 | 14.45 | 14.17 |
| TOTAL | 100.00 | 100.00 | 100.00 | 100.00 |
| Total C8 olefin conversion | 73.43 | 68.97 | 56.85 | 53.60 |
| C8-paraffin selectivity | 47.20 | 44.68 | 44.15 | 46.64 |
| Cracking to C3 and C5 | 50.57 | 55.32 | 53.68 | 53.36 |
| Ratio of Isobutane/C8 = (mol) | 75.09 | 78.55 | 65.67 | 72.64 |
| Isobutane conversion | 0.98 | 0.96 | 0.84 | 0.78 |
| H2 balance | −5.83 | 0.19 | −2.89 | 2.92 |
| Hours on Olefin | 24 | 41 | 48 | 65 |

EXAMPLES 24-27

In Examples 20-23, activated carbon Norit PK1-3 (8/20 mesh, 4 ml) was preheated in helium and pretreated with isobutane for several hours (0.962 LHSV) before introducing 4-methylpentene-1 (Aldrich) from a separate pump (0.038 LHSV). The reaction was carried out at 400° C. and 800 psig. The entire reactor effluent was collected as a liquid under pressure and analyzed by GC using a high pressure syringe for sample transfer. Techniques including GC/MS, bromination/GC, and comparison with available standards were used to identify the reaction products. Example 25 is a pre-run for temperature increase to 425° C. (see Example 24) from 400° C. Example 27 is a pre-run for increasing olefin content from pure isobutane pretreatment.

TABLE 10

Isobutane/4-Methylpentene-1 Over Activated Carbon at Different Times on Stream

|  | Ex. 24 | Ex. 25 | Ex. 26 | Ex. 27 |
|---|---|---|---|---|
| Temperature (°C.) | 425 | 400 | 400 | 400 |
| Pressure (psig) | 800 | 800 | 800 | 800 |
| Normalized Products |  |  |  |  |
| C3 | 6.65 | 4.53 | 4.14 | 3.74 |
| Isobutylene | 29.63 | 22.66 | 23.65 | 31.44 |
| 4-Methylpentene-1 | 2.52 | 4.28 | 3.26 | 0.89 |
| Other C6-olefins | 16.71 | 23.32 | 23.94 | 15.95 |
| 2-Methylpentane | 43.19 | 44.50 | 44.30 | 46.21 |
| Other C6-paraffins | 1.29 | 0.71 | 0.71 | 1.77 |
| C7-plus | 0.00 | 0.00 | 0.00 | 0.00 |
| TOTAL | 100.00 | 100.00 | 100.00 | 100.00 |
| Total C6-olefin conversion | 71.73 | 63.10 | 63.16 | 74.30 |
| C6-paraffin selectivity | 89.03 | 93.52 | 94.26 | 96.23 |
| Cracking to C3 | 10.97 | 6.48 | 5.74 | 3.77 |
| Isobutane/C6 = (mol) | 44.39 | 45.81 | 46.19 | 68.29 |
| Isobutane conversion | 1.42 | 0.96 | 1.00 | 1.02 |
| H2 balance | 2.23 | −29.89 | −23.93 | 0.64 |

TABLE 10-continued

Isobutane/4-Methylpentene-1 Over Activated Carbon at Different Times on Stream

|  | Ex. 24 | Ex. 25 | Ex. 26 | Ex. 27 |
|---|---|---|---|---|
| Hours on Olefin | 67 | 53 | 44 | 20 |

EXAMPLES 28-34

In Examples 28-34, activated carbon Norit PK1-3 (8/20 mesh, 4 ml) was preheated in helium and pretreated with isobutane for several hours (0.962 LHSV) as in the preceeding Examples 20-23 before introducing 2-methylpentene-1 (Aldrich) from a separate pump (0.038 LHSV). Initial reactor conditions were 400° C. and 800 psig. The entire reactor effluent was collected as a liquid under pressure and analyzed by GC using a high pressure syringe for sample transfer. Techniques including GC/MS, bromination/GC, and comparison with available standards were used to identify the reaction products. Example 28 is a pre-run for increasing the olefin content from pure isobutane pretreatment. Example 33 is a pre-run for increasing olefin flow from 0.15 ml/hr. to 0.32 ml/hr.

TABLE 11

Isobutane/2-Methylheptene-1 at 400° C. (800 psig) Over Activated Carbon

|  | Ex. 28 | Ex. 29 | Ex. 30 | Ex. 31 | Ex. 32 | Ex. 33 | Ex. 34 |
|---|---|---|---|---|---|---|---|
| Normalized Products |  |  |  |  |  |  |  |
| Isobutylene | 20.07 | 16.10 | 15.96 | 15.55 | 16.68 | 11.46 | 6.91 |
| n-Butane | 5.01 | 3.80 | 3.28 | 3.75 | 4.01 | 3.11 | 1.67 |
| 2-Methylheptenes | 1.38 | 3.22 | 4.89 | 7.44 | 10.48 | 26.19 | 38.11 |
| Other C8 olefins | 0.00 | 3.01 | 4.46 | 6.22 | 6.27 | 11.00 | 10.91 |
| 2-Methylheptane | 62.76 | 63.32 | 61.98 | 58.68 | 55.19 | 39.23 | 36.38 |
| Other C8-paraffins | 0.00 | 0.00 | 0.00 | 0.00 | 0.00 | 0.00 | 0.00 |
| C8-aromatics | 10.79 | 10.55 | 9.43 | 8.35 | 7.36 | 9.01 | 6.01 |
| C9-plus | 0.00 | 0.00 | 0.00 | 0.00 | 0.00 | 0.00 | 0.00 |
| Total | 100.00 | 100.00 | 100.00 | 100.00 | 100.00 | 100.00 | 100.00 |
| Total C6-olefin conversion | 98.31 | 92.70 | 88.80 | 84.07 | 80.02 | 58.33 | 46.53 |
| C6-paraffin selectivity | 76.76 | 78.63 | 82.11 | 79.91 | 80.78 | 74.06 | 83.80 |
| Cracking selectivity to C4 | 9.05 | 7.29 | 4.45 | 7.85 | 7.64 | 7.66 | 1.31 |
| C8-aromatics selectivity | 14.19 | 14.08 | 13.43 | 12.24 | 11.58 | 18.29 | 14.89 |
| Isobutane/C8 = (mol) | 77.38 | 50.77 | 52.87 | 48.02 | 54.66 | 35.51 | 23.40 |
| Isobutane conversion | 0.61 | 0.72 | 0.70 | 0.73 | 0.70 | 0.70 | 0.62 |
| H2 balance | 12.17 | 0.81 | −1.20 | −5.03 | −0.18 | 21.24 | −9.58 |
| Hours on Olefin | 15 | 24 | 39 | 47 | 63 | 71 | 87 |

EXAMPLES 35-39

The procedure of Examples 28-34 was repeated using 2-methylheptene-1 (Aldrich). Initial reactor conditions were 400° C. and 800 psig. Results are summarized below in Table 12, showing high selectivity for hydrogen transfer between isobutane and 2-methylheptene-1 with relatively low cracking activity.

TABLE 12

| Temperature (°C.) | 400 | 400 | 400 | 400 | 400 |
|---|---|---|---|---|---|
| Pressure (psig) | 800 | 800 | 800 | 800 | 800 |
| Normalized Products |  |  |  |  |  |
| C3 | 4.13 | 2.53 | 2.64 | 2.39 | 2.40 |
| Isobutylene | 43.75 | 33.25 | 29.14 | 24.14 | 23.17 |
| 2-Methylpentene-1 | 1.05 | 3.04 | 5.02 | 7.75 | 9.07 |
| Other C6-olefins | 1.99 | 6.53 | 11.34 | 17.95 | 22.50 |
| 2-Methylpentane | 47.51 | 52.72 | 50.43 | 46.89 | 42.06 |
| Other C6-paraffins | 1.57 | 1.94 | 1.44 | 0.88 | 0.82 |
| C7-plus | 0.00 | 0.00 | 0.00 | 0.00 | 0.00 |
| TOTAL | 100.00 | 100.00 | 100.00 | 100.00 | 100.00 |
| Total C6-olefin | 94.06 | 84.91 | 75.98 | 64.93 | 57.52 |

TABLE 12-continued

| | | | | | |
|---|---|---|---|---|---|
| conversion | | | | | |
| C6-paraffin selectivity | 99.80 | 99.13 | 97.93 | 98.05 | 97.97 |
| Cracking to C3 | 0.20 | 0.87 | 2.07 | 1.95 | 2.03 |
| Isobutane/C6 = (mol) | 146.19 | 59.57 | 53.88 | 46.56 | 48.08 |
| Isobutane conversion | 0.85 | 1.28 | 1.15 | 1.02 | 0.94 |
| H2 balance | 26.94 | −7.02 | −15.92 | −28.85 | −20.51 |
| Hours on Olefin | 16 | 24 | 40 | 48 | 64 |

Changes and modifications in the specifically described embodiments can be carried out without departing from the scope of the invention which is intended to be limited only by the scope of the appended claims.

What is claimed is:

1. A process for producing a selected paraffin from a reaction mixture containing
   (i) an acceptor olefin having the carbon backbone structure of said selected paraffin;
   (ii) a donor paraffin having a carbon backbone structure different from that of said selected paraffin;
   (iii) less than about 10 mole percent molecular hydrogen; which process comprises contacting said reaction mixture with a heterogeneous catalyst comprising porous carbon in the absence of added catalytic metal to convert at least a portion of said acceptor olefin to said selected paraffin and to dehydrogenate at least a portion of said donor paraffin.

2. The process of claim 1 wherein said reaction mixture is essentially free of added molecular hydrogen.

3. The process of claim 1 wherein said heterogeneous catalyst comprises a substantially nonacidic substrate.

4. The process of claim 1 wherein said heterogeneous catalyst comprises a substantially inert substrate.

5. The process of claim 1 wherein said porous carbon is derived from a plant source.

6. The process of claim 5 wherein said plant source is selected from the group consisting of coconut shell and peat.

7. The process of claim 1 wherein said active carbon is derived from a mineral source.

8. The process of claim 7 wherein said active carbon is derived from petroleum coke.

9. The process of claim 1 wherein said active carbon is derived from a synthetic source.

10. The process of claim 1 wherein reaction conditions include temperature above about 300° C.

11. The process of claim 10 wherein reaction conditions include temperature of from about 350° C. to about 500° C.

12. The process of claim 1 wherein said acceptor olefin is the product of a dimerization or oligomerization reaction.

13. The process of claim 1 wherein said acceptor olefin is the byproduct of a catalytic hydrocarbon upgrading process.

14. The process of claim 1 wherein said active carbon is activated by treatment with a fluorine-containing compound.

15. The process of claim 14 wherein said fluorine-containing compound is HF.

16. The process of claim 1 wherein said active carbon is activated by treatment with at least one selected from the group consisting of phosphoric acid, and sulfuric acid.

17. The process of claim 1 wherein said active carbon is activated by treatment with steam.

18. The process of claim 1 wherein said active carbon is activated by treatment with hydrogen, carbon oxides, or mixtures thereof.

* * * * *